(12) United States Patent
Ovaa et al.

(10) Patent No.: US 9,079,941 B2
(45) Date of Patent: Jul. 14, 2015

(54) MEANS AND METHODS FOR BREAKING NONCOVALENT BINDING INTERACTIONS BETWEEN MOLECULES

(75) Inventors: Huib Ovaa, Amsterdam (NL); Antonius Nicolaas Maria Schumacher, Haarlem (NL)

(73) Assignees: Het Nederlands Kanker Instituut, Amsterdam (NL); Stichting Sanquin Bloedvoorziening, Amsterdam (NL)

( * ) Notice: Subject to any disclaimer, the term of this patent is extended or adjusted under 35 U.S.C. 154(b) by 1985 days.

(21) Appl. No.: 11/883,119

(22) PCT Filed: Jan. 25, 2006

(86) PCT No.: PCT/NL2006/000038
§ 371 (c)(1),
(2), (4) Date: Oct. 10, 2007

(87) PCT Pub. No.: WO2006/080837
PCT Pub. Date: Aug. 3, 2006

(65) Prior Publication Data
US 2008/0145378 A1    Jun. 19, 2008

(30) Foreign Application Priority Data
Jan. 25, 2005 (EP) .................................... 05075196

(51) Int. Cl.
C07K 14/74    (2006.01)
C07K 14/005   (2006.01)

(52) U.S. Cl.
CPC ......... *C07K 14/005* (2013.01); *C07K 14/70539* (2013.01); *C12N 2760/16122* (2013.01)

(58) Field of Classification Search
None
See application file for complete search history.

(56) References Cited

FOREIGN PATENT DOCUMENTS

| WO | WO 03/016512 A | 2/2003 |
|----|----------------|--------|
| WO | WO 2004/007528 A | 1/2004 |
| WO | WO 2006/080837 A2 | 8/2006 |

OTHER PUBLICATIONS

Celie et al (J.Am. Chem. Soc. 2009, 131: 12298-12304).*
Rodenko et al (Nature Protocols, 2006, 1(3): 1120-1132).*
PCT International Search Report, PCT/NL2006/000038, dated Jul. 26, 2006, pp. 1-5.
PCT International Preliminary Examination Report, PCT/NL2005/000038, dated Jan. 26, 2007, pp. 1-6.
Rodenko, et al.; Generation of peptide-MHC class I compleses through UV-mediated ligand exchange; Nature Protocols; vol. 1 No. 2; 2006, pp. 1120-1131.
Schumacher; et al. Peptide selection by MHC class I molecules; Nature, vol. 350, Apr. 25, 1991; pp. 703-706.
Whelan, et al.; Specificity of CTL Interactions with PeptideMHC Class I Tetrameric Complexes is Temperature Dependent; The Journal of Immunology; 1999, 163: 4342-4348.
Zhao, et al.; Direct and GTP-dependent interaction of ADP ribosylation factor 1 with coatomer subunitβ; Proc. Natl. Acad. Sci.; vol. 94, Apr. 1997, 4418-4423.
O'Conner, et al.; Abstract; Efficient Synthesis of photocleavable amino acid; eNitrophenylglycine;23$^{rd}$ National Meeting of the American Chemical Society, Chicago, IL Mar. 2007 2 pages.
The 2005 Midwinter Conference of Immunologists at Asilomar, Jan. 22, 2005, <.midwconfimmunol.org/element/filemgr_repository/Schumacher.pdf> (retrieved on Mar. 3, 2005), one page.
The 2005 Midwinter Conference of Immunologists at Asilomar, Jan. 22, 2005, <http://.midwconfimmunol.org/element/filemgr_repository/Schumacher.pdf> (retrieved on Mar. 3, 2005).
Peng et al., Synthesis and characterization of photolabile choline precursors as reversible inhibitors of cholinesterase: Release of choline in the microsecond time range, Journal of Organic Chemistry 1996 United States, pp. 185-191, vol. 61, No. 1.
Schumacher et al., Direct Binding of Peptide to Empty MHC Class I Molecules of Intact Cells and In-Vitro, Cell, pp. 563-568, vol. 62, No. 3, 1990.
Toebes et al., Design and use of conditional MHC class I ligands, Nature Medicine, Feb. 2006, pp. 246-251, vol. 12, No. 2.
Bosques et al., Photolytic Control of Peptide Self-Assembly, J. Am. Chem. Soc., pp. 7530-7531, vol. 125, No. 25.
Brusic et al., Prediction of promiscuous peptides that bind HLA class I molecules, Immunology and Cell Biology, 2002, pp. 280-285, vol. 80.
Grewer et al., Abstract, A new photolabile precursor of glycine with improved properties: A tool for chemical kinetic investigations of the glycine receptor, Biochemistry, 2000, pp. 2063-2070, vol. 39, No. 8.
Hart et al., Abstract, Utility of azapeptides as major histocompatibility complex class II protein ligands for T-cell activation, J. Med. Chem, 2001, pp. 3700-3709, vol. 44, No. 22.
Kumar et al., Protein scissors: Photocleavage of proteins at specific locations, Proc. Indian Acad. Sci., Dec. 2002, pp. 579-592, vol. 114, No. 6.
Penner et al., Comparative oxidations of tyrosines and methionines in transferrins: human serum transferrin, human lactotransferrin, and chicken ovotransferrin, Arch. Biochem. Biophys. 1983, pp. 740-747, vol. 225, No. 2.

(Continued)

*Primary Examiner* — Gerald R Ewoldt
*Assistant Examiner* — Marianne Dibrino
(74) *Attorney, Agent, or Firm* — TraskBritt, P.C.

(57) ABSTRACT

The present invention concerns multimeric proteinaceous molecules comprising at least two members that bind each other via a region of noncovalent interaction, wherein a first of the members comprises a conditionally reactive group that, when activated, cleaves a covalent bond within the first member. Cleavage of the covalent bond results in a reduction in the binding strength with which the at least two members bind to each other via the region of noncovalent interaction. The reduction in the binding strength can result in the separation of the members under mild conditions.

11 Claims, 12 Drawing Sheets

(56) References Cited

OTHER PUBLICATIONS

Thaisrivongs et al., Abstract, Inhibitors of the protease from human immunodeficiency virus: design and modeling of a compound containing a dihydroxyethylene isostere insert with high binding affinity and effective antiviral activity, J. Med. Chem, 1991, pp. 2344-2356, vol. 34, No. 8.

Yang et al., Beta-Amino Alcohol Properfumes, Helvetica Chimica Acta, 2003, pp. 2928-2936, vol. 86.

Altman et al., Phenotypic Analysis of Antigen-Specific T Lymphocytes, Science, Oct. 4, 1996, pp. 94-96, vol. 274.

Soen et al., Detection and Characterization of Cellular Immune Responses Using Peptide—MHC Microarrays, PLOS Biology, 2003, pp. 429-438, vol. 1, No. 3.

Parmiani et al., Heat Shock Proteins and Their Use as Anticancer Vaccines, Clinical Cancer Research, 2004, pp. 8142-8146, vol. 10.

Bakker et al. (2008) (PNAS, 2008, 105(10):3825-30).

Brackenridge et al. (2011) (J. Virol., 2011, 85(11):5415-22).

Frickel et al. (2008) (J. Infect. Dis., 2008, 198(11):1625-33).

Grotenbreg et al. (2008) (PNAS, 2008, 105(10):3831-36).

Rodenko et al. (2009) (J. Am. Chem. Soc., 2009, 131(34):12305-13).

Toebes et al. (2006) (Nat. Med., 2006, 12(2):246-51).

\* cited by examiner

SEQUENCE LISTING

```
<160> NUMBER OF SEQ ID NOS: 7

<210> SEQ ID NO 1
<211> LENGTH: 9
<212> TYPE: PRT
<213> ORGANISM: Influenza A virus

<400> SEQUENCE: 1

Ala Met Asp Ser Asn Thr Leu Glu Leu
1               5

<210> SEQ ID NO 2
<211> LENGTH: 9
<212> TYPE: PRT
<213> ORGANISM: Influenza A virus

<400> SEQUENCE: 2

Gly Ile Leu Gly Phe Val Phe Thr Leu
1               5

<210> SEQ ID NO 3
<211> LENGTH: 9
<212> TYPE: PRT
<213> ORGANISM: Influenza A virus
<220> FEATURE:
<221> NAME/KEY: misc_feature
<222> LOCATION: (4)..(4)
```

<223> OTHER INFORMATION: Xaa can be either Glycine or 3-amino-3-(2-
      nitrophenyl)propionic acid

<400> SEQUENCE: 3

Gly Ile Leu Xaa Phe Val Phe Thr Leu
1               5

<210> SEQ ID NO 4
<211> LENGTH: 9
<212> TYPE: PRT
<213> ORGANISM: Influenza A virus
<220> FEATURE:
<221> NAME/KEY: misc_feature
<222> LOCATION: (8)..(8)
<223> OTHER INFORMATION: Xaa can be either threonine or 3-amino-3-(2-
      nitrophenyl)propionic acid

<400> SEQUENCE: 4

Gly Ile Leu Gly Phe Val Phe Xaa Leu
1               5

<210> SEQ ID NO 5
<211> LENGTH: 10
<212> TYPE: PRT
<213> ORGANISM: Influenza A virus
<220> FEATURE:
<221> NAME/KEY: misc_feature
<222> LOCATION: (6)..(6)
<223> OTHER INFORMATION: Xaa is cysteine labeled with
      tetramethylrhodamine

<400> SEQUENCE: 5

Phe Leu Pro Ser Asp Xaa Phe Pro Ser Val
1               5                   10

<210> SEQ ID NO 6
<211> LENGTH: 9
<212> TYPE: PRT
<213> ORGANISM: Influenza A virus
<220> FEATURE:
<221> NAME/KEY: MISC_FEATURE
<222> LOCATION: (3)..(3)
<223> OTHER INFORMATION: Residues 3 (xaa) is a modified Leu. The linking
      -CO- has been replaced by CH(OH).
<220> FEATURE:
<221> NAME/KEY: MISC_FEATURE
<222> LOCATION: (3)..(4)
<223> OTHER INFORMATION: Residues 3 and 4 are modified residues linked
      by a non-peptidyl bond. They form a dihydroxyethylene isostere in
      which the -CO-NH connecting groups are replaced by [CH(OH)CH(OH)].
      e.g. IUPAC name for this is Leu-(Psi)[CH(OH)CH(OH)]-Gly.
<220> FEATURE:
<221> NAME/KEY: MISC_FEATURE
<222> LOCATION: (4)..(4)
<223> OTHER INFORMATION: Residues 4 (xaa) is a modified Gly. The linking
      -NH- group has been replaced by CH(OH).

<400> SEQUENCE: 6

Gly Ile Xaa Xaa Phe Val Phe Thr Leu
1               5

<210> SEQ ID NO 7
<211> LENGTH: 9
<212> TYPE: PRT
<213> ORGANISM: Influenza A virus
<220> FEATURE:
<221> NAME/KEY: MISC_FEATURE
<222> LOCATION: (8)..(8)
<223> OTHER INFORMATION: Xaa is 4-amino-2,3-dihydroxybutanoic acid

```
<400> SEQUENCE: 7

Gly Ile Leu Gly Phe Val Phe Xaa Leu
1               5
```

MEANS AND METHODS FOR BREAKING NONCOVALENT BINDING INTERACTIONS BETWEEN MOLECULES

CROSS-REFERENCE TO RELATED APPLICATIONS

This is a national phase entry under 35 U.S.C. §371 of International Patent Application PCT/NL2006/000038, filed Jan. 25, 2006, published in English as International Patent Publication WO 2006/080837 A2 on Aug. 3, 2006, which claims the benefit under 35 U.S.C. §119 of European Patent Application Serial No. 05075196.5 filed Jan. 25, 2005, the entire contents of each of which are hereby incorporated herein by this reference.

TECHNICAL FIELD

The invention relates to the field of binding molecules. The invention, in particular, relates to means and methods for breaking noncovalent interactions between members of a multimeric proteinaceous molecule.

BACKGROUND

Noncovalent interactions are very important, especially in the field of biology. Noncovalent bonding holds the two strands of the DNA double helix together (hydrogen bonds), folds polypeptides into such secondary structures as the alpha helix and the beta conformation, enables enzymes to bind to their substrate, enables antibodies to bind to their antigen, enables transcription factors to bind to each other, enables transcription factors to bind to DNA, enables proteins (e.g., some hormones) to bind to their receptor, and permits the assembly of such macromolecular machinery as ribosomes, actin filaments, microtubules and many more.

There are three principal kinds of noncovalent forces; i.e., ionic interactions, hydrophobic interactions and hydrogen bonds.

Ionic Interactions as Exemplified by Protein Interactions

At any given pH, proteins have charged groups that may participate in binding them to each other or to other types of molecules. For example, negatively charged carboxyl groups on aspartic acid (Asp) and glutamic acid (Glu) residues may be attracted by the positively charged protonated amino groups on lysine (Lys) and arginine (Arg) residues.

Ionic interactions are highly sensitive to changes in pH. As the pH drops, H+ bind to the carboxyl groups (COO—) of aspartic acid (Asp) and glutamic acid (Glu), neutralizing their negative charge, and H+ bind to the unoccupied pair of electrons on the N atom of the amino (NH2) groups of lysine (Lys) and arginine (Arg), giving them a positive charge. The result: Not only does the net charge on the molecule change (it becomes more positive), but many of the opportunities that its side chain or main chain groups have for ionic (electrostatic) interactions with other molecules and ions are altered. As the pH rises, H+ are removed from the COOH groups of Asp and Glu, giving them a negative charge (COO—), and H+ are removed from the NH3+ groups of Lys and Arg, removing their positive charge. The result: the net charge on the molecule changes (it becomes more negative) and, again, many of the opportunities its side chain or main chain groups have for electrostatic interactions with other molecules or ions are altered.

Ionic interactions are also sensitive to salt concentration. Increasing salt concentration reduces the strength of ionic binding by providing competing ions for the charged residues.

Hydrophobic Interactions as Exemplified by Protein Interactions

The side chains (R groups) of such amino acids as phenylalanine and leucine are nonpolar and, hence, interact poorly with polar molecules like water. For this reason, most of the nonpolar residues in globular proteins are directed towards the interior of the molecule, whereas such polar groups as aspartic acid and lysine are on the surface exposed to the solvent. When nonpolar residues are exposed at the surface of two different molecules, it is energetically more favorable for their two "oily" nonpolar surfaces to approach each other closely, displacing the polar water molecules between them.

The strength of hydrophobic interactions is not appreciably affected by changes in pH or in salt concentration.

Hydrogen Bonds as Exemplified by Protein Interactions

Hydrogen bonds can form whenever a strongly electronegative atom (e.g., oxygen, nitrogen) approaches a hydrogen atom, which is covalently attached to a second strongly electronegative atom.

Some common examples: between the —C=O group and the H—N— groups of separated peptide bonds in proteins (giving rise to the alpha helix and beta configuration); between —C=O groups and hydroxyl (H—O—) groups in serine and threonine residues and the SH groups of cysteine of proteins and in sugars.

It is a characteristic of noncovalent interactions that they are individually weak but collectively strong. All three forms of noncovalent interactions are individually weak (in the order of 5 kcal/mole) as compared with a covalent bond (with its 90-100 kcal/mole of bond energy). There are types of bonds with an intermediary bond energy (i.e., between 15 and 70 kcal/mole). For the present invention, such types of bonds are considered noncovalent if they are by themselves insufficient to associate two proteinaceous molecules in a certain environment. In other words, noncovalent bonds are those of which a substantial number of interactions working together are needed to hold structures together. The limited strength that these interactions do have requires that the interacting groups can approach each other closely (an angstrom or less).

Thus, a multimer comprising two or more members is, in one aspect, said to be held together by noncovalent bonds if the two or more members are linked by at least three, and preferably at least five, bonds that each have a bond energy of less than 90-100 kcal/mole. A typical cysteine disulfide bridge linking two protein chains has a bond energy of about 65 kcal/mole. However, the strength of this bond is very dependent on the reducing/oxidizing environment. Thus, for the present invention, a multimer is said to be held together by noncovalent bonds when the bonds that link the two or more member chains each have a bond energy of less than 65 kcal/mole, and typically less than 20 kcal/mole. Usually, each of the bonds has a binding energy of around 5 kcal/mole. Thus, two or more members in a multimer that are held together by noncovalent bonds have a substantial number of noncovalent interactions working together to hold the structures together and have a surface topography that enables substantial areas of the at least two interacting surfaces to approach each other closely; that is, they must fit each other.

DISCLOSURE OF THE INVENTION

The present invention utilizes the characteristic that many weak bonds are required to keep the structures in a multimeric proteinaceous molecule together via a region of non-covalent interaction.

In the present invention, at least one member involved in the noncovalent interaction in the multimer is broken up in at least two new members by severing at least one covalent bond in the at least one member of the multimer. The cleavage of one covalent bond results in a multimer that has one more member than the original multimer. Cleavage of two covalent bonds results in a multimer that has two more members, etc. The cleaving of at least one covalent bond in the multimer results in a decrease of the number of noncovalent interactions per member in the multimer.

In the present invention, this reduction is used to cause dissociation of at least one member from the multimer.

In the present invention, the cleavage of a covalent bond is used to reduce the number of noncovalent bonds per member in the multimer such that the noncovalent bonds are insufficient to maintain the integrity of the multimer, or the cleavage of a covalent bond is used to alter the conformation of the member in which this modification has occurred and thereby causing the release of at least one member from the multimer. After release of the at least one member, the resulting members can be monomers, multimers or a combination thereof. Cleavage of a covalent bond in a peptide can be achieved by enzymatic means, chemical means or physical means. Cleavage of a covalent bond as used in the invention is preferably chemical or physical, i.e., preferably non-enzymatic. More preferably, cleavage of a bond is chemical- or light-inducible. Further preferred is that a covalent bond is cleaved in a peptide backbone. A covalent bond that is preferably cleaved is a bond positioned next to a peptide bond (thus, a bond on the other side of the nitrogen atom).

As used herein, the term "multimeric proteinaceous molecule" refers to a proteinaceous molecule that contains two or more members that are associated with each other via a region of noncovalent interaction. At least two members are only linked to each other via noncovalent interactions and not via covalent interactions. The terms "multimeric proteinaceous molecule" and "multimeric protein" are interchangeably used in the description. The multimeric proteinaceous molecule of the present invention typically contains at least one polypeptide.

The term "region of noncovalent interaction" refers to a region where two or more members associate and interact with each other via at least three, and preferably at least five, noncovalent bonds. This region of noncovalent interaction preferably does not comprise a covalent bond linking two or more members to each other. It is clear that not all atoms participate in non-covalent interaction in the region. Similarly, if the region is a region where two (poly) peptides are associated, it is not required that all amino acids participate in noncovalent interaction in the region.

A "monomer" is used herein to refer to a molecule wherein the building blocks are still covalently associated with each other when all noncovalent bonds are broken. More than one monomer in the multimer may be the same or different from each other.

The term "member" is used herein to refer to an entity of the multimer that is noncovalently linked to another member of the multimer. These two members are not linked via a covalent bond. A member is preferably, but not necessarily a proteinaceous molecule. A member is typically, but not necessarily, a (poly)peptide.

A multimeric proteinaceous molecule of the invention is preferably a multimeric protein. A multimeric protein according to the invention preferably comprises a first member comprising a peptide and at least a second member comprising a (poly)peptide and/or a protein. The peptide preferably comprises the conditionally reactive group.

A proteinaceous molecule comprises at least two amino acids in peptidic linkage with each other. It typically contains at least eight amino acids, or functional equivalents thereof, in peptidic linkage with each other.

In the present invention, a polypeptide contains at least 50 amino acids, or functional equivalents thereof, that are linked to each other via peptide bonds. In its unfolded state, the polypeptide is typically a linear molecule but can be (partly) circular. A peptide typically contains between four and 49 amino acids that are linked to each other via peptide bonds. Preferably, a peptide contains from three to 49 amino acids, preferably from three to 30, more preferably from three to 20 amino acids.

A (poly)peptide as used herein can comprise any amino acid or amino acid chain. An amino acid can be a natural or synthetic amino acid such as, for instance, an alpha, beta, or gamma or higher (omega) amino acid, i.e., including one, two, three, or more carbon spacings between amino groups and carboxylic acids. An amino acid (chain) can be a natural amino acid (chain) or a synthesized amino acid (chain) or a combination thereof. A peptide is a natural peptide or a synthesized peptide or a combination thereof. Again, in its unfolded state, a peptide is typically linear, but can be (partly) circular. A peptide typically does not have a dominant tertiary structure. It typically accommodates a range of tertiary structures. A peptide as used in the invention is typically easily dissolvable in diverse solvents. Such solvents are, for instance, physiological solutions, such as a physiological sodium chloride solution.

An antigenic peptide that is a ligand for an MHC molecule typically has between eight and 25 amino acids that are linked via peptide bonds. (Poly)peptides may or may not be modified. Typical modifications include those as produced by the cellular machinery, such as glycan addition and phosphorylation. However, other types of modification are also within the scope of the invention.

A functional equivalent of an amino acid is a molecule that can replace one or multiple amino acids in an amino acid chain. The functional equivalent is preferably capable of forming bonds with amino acids in two separate positions such that it can form an internal part of a (poly)peptide or peptidomimetic chain. The functional equivalent does not have to have a natural counterpart. Such a functional equivalent can be incorporated into a peptide or (poly)peptide of the invention.

In one aspect of the present invention, the covalent bond that is cleaved is preferably a backbone bond that links two amino acids, or derivative/analogue thereof, in one member chain. Cleavage of the covalent bond is preferably achieved by incorporating a conditionally reactive group into the member, preferably a peptide member, in which at least one covalent bond needs to be broken. In the present invention, the term "conditionally reactive group" is used to refer to a reactive group that is incorporated into the member. The term "conditionally" is used to reflect that the reactive group can be activated conditionally, i.e., in response to a signal or trigger. The number of conditionally reactive groups can be varied at will. A conditionally reactive group can also be placed at an exact position in the member, for instance, by incorporating it into a nascent (poly)peptide chain. In one embodiment, the one or more conditionally reactive groups are placed such that the covalent bond is broken in a region of noncovalent interaction of the member with at least one other member in the multimer. In another embodiment, the one or more conditionally reactive groups are placed such that the preferred conformation of the ligand (e.g., member) is altered such that the affinity of the interaction with other members of the multimer is reduced.

In one aspect, the invention provides a multimeric proteinaceous molecule comprising at least two members that bind each other via a region of noncovalent interaction, wherein at least one of at least two members comprises a conditionally reactive group that, when activated, cleaves a covalent bond within the member, thereby cleaving the member into at least two smaller members, which in turn reduces the strength of noncovalent interaction in the region. Cleavage of a covalent bond in a member results in more folding freedom for the resulting chains, thereby reducing the strength of any noncovalent interaction that one or more of the resulting chains have in the multimer. In a preferred embodiment, the member is cleaved within the region of noncovalent interaction. This results in the highest reduction of the strength of the noncovalent interaction in the region. The bond that is cleaved by the conditionally reactive group can be selected by appropriately positioning the reactive group in the peptide chain. Cleavage of the member results in peptide chains of a smaller size. It is preferred that the longest of the resulting peptides is at least 20%, and preferably at least 30%, shorter than the member.

The invention further provides a multimeric proteinaceous molecule (a multimer) comprising at least two members that bind each other via a region of noncovalent interaction, wherein at least one of at least two members comprises a (poly)peptide chain with a conditionally reactive group and wherein, when the reactive group is activated, a covalent bond within the member is broken resulting in cleavage of the (poly)peptide into at least two smaller (poly)peptides, thereby reducing the strength of the noncovalent interaction.

In a preferred embodiment, the conditionally reactive group comprises a light-sensitive or periodate-sensitive group. In these embodiments, the conditional step that activates the reactive group is either the presence or absence of light within a defined wavelength range or the exposure of the periodate-sensitive group to periodate. In a preferred embodiment, the light-sensitive reactive group is a UV-sensitive group. The conditionally reactive group is preferably incorporated into a (poly)peptide. In a preferred embodiment, the UV-sensitive group comprises 3-amino-3(2-nitrophenyl)propionic acid (Carlos J. Bosques and Barbara Imperiali, Journal of the American Chemical Society 2003, vol. 125, pp. 7530-7531). This amino acid is commercially available from Alpha Aesar and is to be protected with an Fmoc-protecting group in order to be compatible with solid phase peptide synthesis, or ortho-nitrophenyl-glycine (Alvie L. Davis, David R. Smith and Tommy J. McCord, Synthesis and Microbiological Properties of 3-amino-1-hydroxy-2-indolinone and related compounds, Journal of Medicinal Chemistry 1973, vol. 16, pp. 1043-1045), or a functional equivalent of such molecules. A functional equivalent of 3-amino-3-(2-nitrophenyl)propionic acid is 3-amino-3(4-nitrophenyl)propionic acid. A functional equivalent of ortho-nitrophenyl-glycine is para-nitrophenyl-glycine.

In another preferred embodiment, the periodate-sensitive group comprises a 1,2-dihydroxy moiety or a functional equivalent thereof. There are alternative systems that are equivalent to the periodate and 1,2-dihydroxy system. Such systems are 1-amino-2-hydroxy systems and polyols, carbohydrates, sugar-amino acid hybrids containing a periodate-cleavable site. Dihydroxyethylene peptide isosters are described in Suvit Thaisrivongs, Alfredo G. Tomasselli, Joseph B. Moon, John Hui, Thomas J. McQuade, Steve R. Turner, Joseph W. Strohbach, W. Jeffrey Howe, W. Gary Tarpley, and Robert L. Heinrikson, "Inhibitors of the protease from human immunodeficiency virus: design and modeling of a compound containing a dihydroxyethylene isostere insert with high binding affinity and effective antiviral activity," Journal of Medicinal Chemistry 1991, vol. 34, pp. 2344-2356; Suvit Thaisrivongs, Steve R. Turner, Joseph W. Strohbach, Ruth E. TenBrink, W. Gary Tarpley, Thomas J. McQuade, Robert L. Heinrikson, Alfredo G. Tomasselli, Joseph B. Moon, John O. Hui, W. Jeffrey Howe, "Inhibitors of the protease from human immunodeficiency virus: synthesis, enzyme inhibition, and antiviral activity of a series of compounds containing the dihydroxyethylene transition-state isostere," Journal of Medicinal Chemistry 1993, vol. 36, pp. 941-952; and Iwao Ojima, Hong Wang, Tao Wang and Edward W. Ng, "New approaches to the asymmetric synthesis of dipeptide isosteres via beta-lactam synthon method," Tetrahedron Letters 1998, vol. 39, pp. 923-926. The synthesis of 4-amino-4-deoxy-L-threonic acid (diol-containing amino acid building block), which is another periodate-sensitive compound, is described in James A. Musich and Henry Rapoport, "Synthesis of Anthopleurine, the alarm pheromone from anthopleura elegantissima," Journal of the American Chemical Society 1978, vol. 100, pp. 4865-4872.

The technology can be used for many different proteinaceous molecules interacting with ligands of a proteinaceous nature (multimers). In a preferred embodiment, a multimeric protein of the invention comprises at least two members wherein a first member comprises a peptide comprising the conditionally reactive group and wherein a second member comprises a polypeptide, wherein the first and the second member bind to each other via a region of non-covalent interaction. Preferably, the multimeric protein is a peptide-binding protein, preferably a peptide-presenting protein, and bound peptide. Preferred examples of such peptide-binding proteins are proteins with SH2-SH3 domains, chaperone proteins or major histocompatibility complex molecules. Preferred chaperone proteins are heat shock proteins. Examples of these heat shock proteins are HSP70, gp96, gp110 and calreticulin. Heat shock proteins loaded with antigens (peptides) are, for instance, used to specifically stimulate the immune system. This specific stimulation helps to combat diverse diseases, for instance, disorders caused by the papillomavirus or cancer (see, for instance, Parmiani et al., 2004).

A preferred multimer is a major histocompatibility complex (MHC) molecule or a functional part, derivative and/or analogue thereof. MHC is recognized by T-cells. T-cells play a crucial role in the human immune system and a multitude of strategies has been developed to enhance this natural defense system and boost immunity against pathogens or malignancies. T-cells recognize MHC molecules that have bound a specific ligand and production methods for MHC molecules that have bound a specific ligand are of substantial value. In addition, MHC molecules are also recognized by a series of other receptors providing an additional rationale for the production of ligand-bound MHC molecules. In addition, definition of disease-associated ligands that bind to MHC molecules is of value for both diagnostic and therapeutic purposes.

An important use of ligand-MHC complexes is illustrated by the fact that complexes of ligand-occupied MHC molecules are highly valuable tools in the medical field to identify and quantify specific T-cell populations and evaluate establishment of effective cellular immunity in relation to disease progression. A very large potential for MHC complexes lies in the immune monitoring of clinical trials and approved therapeutic interventions. In addition, MHC complexes can be applied to isolate specific human T-cells for cellular immunotherapy against pathogens or malignancies or to eliminate undesired T-cells from preparations for bone marrow transplantations. In addition, MHC complexes may be used to selectively eliminate undesired specific T-cell populations in T-cell-mediated diseases.

A major obstacle for the effective application of MHC molecules occupied with a defined ligand is the inefficiency of the current production methods. The stability of MHC molecules and, in particular, MHC class I molecules, is low when antigen is not bound. Consequently, MHC molecules are produced primarily in processes in which the ligand is bound during the production process. Exchange of this bound ligand for a ligand of choice has been used, but this process is inefficient because dissociation of ligand is slow under mild conditions (i.e., near neutral pH and physiological salt concentration). Dissociation of bound ligand can be promoted by exposing MHC molecules to more harsh conditions (e.g., acidic or alkaline pH), but this also leads to destabilization of the MHC molecule. Consequently, the technology that is now most widely accepted for the generation of recombinant MHC molecules is the separate production of a batch of ligand-occupied MHC molecules for each single ligand. This results in a very time-consuming and costly production process, yielding small batches specific for only one application. (A. H. Bakker and T. N. Schumacher, "MHC multimer technology: current status and future prospects," Curr. Opin. Immunol. 2005, August; 17(4):428-33, Review.)

MHC molecules can be divided into two classes, MHC class I and class II molecules. Both types of MHC molecules can bind peptides and present them to T-cells. Depending on the MHC molecule, the domains responsible for binding of the peptide have different nomenclatures. Typically, two domains are required for specifically binding a peptide, as exemplified by the alpha1 and alpha2 domains of an MHC class I molecule. These domains are considered a functional part of an MHC molecule. A functional part thus typically contains two of the domains that in an MHC molecule are involved in binding of a peptide. A natural MHC molecule typically contains several other domains that are not directly involved in binding of a peptide. Such domains typically have other functions. For instance, there is a transmembrane domain or a cytosolic domain. In addition, such domains may play a role on the formation of the folded conformation of the peptide-binding domains. Other domains can, like the peptide-binding domains, be extra-cellular. All these other domains share one characteristic. They are not directly involved in peptide binding. Thus, for the present invention, they may be present in a part of an MHC molecule or not, as long as the part comprises at least two of the domains that are involved in peptide binding in an MHC molecule. Preferably, the MHC molecule is a soluble MHC molecule, preferably as described in D. N. Garboczi, D. T. Hung, and D. C. Wiley, HLA-A2-peptide complexes: refolding and crystallization of molecules expressed in *Escherichia coli* and complexed with single antigenic peptides, Proc. Natl. Acad. Sci. U.S.A. 1992 Apr. 15; 89(8):3429-33.

In a preferred embodiment, the MHC molecule is an MHC-complex molecule.

A functional derivative of an MHC molecule is a molecule that is not derived from nature, but that shares at least a peptide-binding property with an MHC molecule in kind, not necessarily in amount. For instance, modified MHC molecules comprising one or more amino acid differences with natural MHC molecules but that retain a peptide-binding function are functional derivatives in the context of the present invention. Similarly, molecules comprising (part of) peptide-binding domains from two or more MHC molecules and that are capable of binding a peptide are also considered functional derivatives. Modifications that are typically tolerated are those that are not in the peptide-binding domains. Other mutations or modifications that are tolerated are in the variable domains of the peptide-binding domains of MHC molecules. Such modifications typically alter the binding specificity of the MHC molecule (i.e., which peptide is bound). Such modifications are, therefore, also considered functional derivatives of MHC molecules of the invention.

Several molecules share the peptide-binding properties of MHC molecules but have evolved to serve a different purpose in the cell. Such molecules are considered functional analogues of an MHC molecule of the present invention. Domains that are involved in (poly)peptide binding can be combined with such domains from MHC molecules. MHC molecules or functional parts, derivatives and/or analogues thereof, may further contain other parts that are not normally associated with MHC molecules. Such other parts may, for instance, comprise labels, tags, association and/or multimerization domains and other elements.

The technology of the present invention can be used to specifically destabilize ligands bound to MHC molecules, or to functional parts, derivatives and/or analogues thereof. Destabilization of the MHC-bound ligands then results in the generation of ligand-free MHC molecules without exposure to harsh conditions. The resulting ligand-free MHC molecules may then be used either in the ligand-free form or may be loaded with one or multiple ligands of choice.

Thus, in a preferred aspect of the present invention, an MHC molecule or a functional part, derivative and/or analogue thereof, comprises a peptide antigen (also referred to as ligand) in the peptide-binding groove of the MHC molecule or a functional part, derivative and/or analogue thereof. The inducible attacking group or conditionally reactive group is preferably present in the peptide antigen as this warrants release of the peptide antigen from the otherwise unmodified MHC molecule or a functional part, derivative and/or analogue thereof. The resultant ligand-free MHC molecules may be used directly or be loaded with one or more other ligands.

To this end, the invention further provides a composition comprising a multimeric protein of the invention. Such a composition can be provided with ligand to be loaded onto the MHC molecule. Thus, further provided is a major histocompatibility complex (MHC) molecule or a functional part, derivative and/or analogue thereof, wherein at least one of the members is a peptide antigen in the peptide-binding groove of the molecule and wherein the peptide antigen comprises the inducible cleavable group or conditionally reactive group. The composition can also comprise a further peptide.

In a preferred embodiment, the further peptide is an antigenic peptide capable of binding in the peptide-binding groove of the MHC molecule, i.e., a ligand for the MHC molecule. The attacking group of the peptide may be induced, thereby resulting in release of the peptide fragments from the multimer. If the further peptide is also present in the composition, this peptide can now take the place of the leaving fragments. The resultant MHC molecule or functional part, derivative and/or analogue thereof is thereby loaded with the further peptide. Thus, the composition contains the newly loaded MHC molecule (or functional part, derivative and/or analogue thereof) and fragments of the leaving peptide.

In another aspect, the invention provides a method for producing an MHC molecule or a functional part, derivative and/or analogue thereof, or an MHC molecule complex comprising a further peptide, comprising producing an MHC molecule comprising a temporary peptide having an inducible cleavable group or conditionally reactive group that, when activated, cleaves the temporary peptide into at least two smaller peptides that exhibit reduced binding affinity for the MHC molecule. The temporary peptide is preferably present in the peptide-binding groove of the MHC molecule or a functional part, derivative and/or analogue of the MHC molecule. The method preferably further comprises activating the cleavable group or conditionally reactive group.

As a result of the activation, the temporary or leaving peptide is cut into smaller peptides (or amino acids), thereby reducing the strength of the noncovalent interaction in the region of noncovalent interaction. This allows the easy removal of the leaving peptide (or fragments thereof) from the MHC molecule or functional part, derivative and/or analogue thereof. Removal does not require harsh conditions and, thus, only minimally interferes with the activity of the molecule, if at all. The free MHC molecule can be provided with a desired peptide. Using a method of the invention, it is possible to produce large amounts of MHC molecule having the leaving peptide. This preparation can subsequently be used to generate MHC molecules comprising a variety of different ligands (antigenic peptides) with a method of the invention. This only requires activation (induction) of the cleavable group that cleaves the leaving peptide, which allows for the exchange with the desired antigenic peptide.

Induction of the cleavable group or conditionally reactive group, the dissociation of leaving peptide fragments and association of the desired peptide to the MHC molecule or functional part, derivative and/or analogue thereof, can be performed in one step. Thus, the invention further provides a method of the invention further comprising incubating the MHC molecule or functional part, derivative and/or analogue thereof, with the desired peptide under conditions that effectively removes cleaved temporary peptide from the MHC molecule.

Further provided is a method of the invention, further comprising detecting binding of the desired peptide to the MHC molecule. This aspect is, for example, useful for diagnostic purposes. Binding can be detected in various ways, for instance, via T-cell receptor or antibody specific for the peptide presented in the context of the MHC molecule. Binding is preferably detected by detecting a label that is associated with the peptide. This can be done by tagging the peptide with a specific binding molecule, such as biotin, that can subsequently be visualized via, for instance, labeled streptavidin or analogues thereof.

In a preferred embodiment, the peptide comprises the label. In this way, any peptide bound to the MHC molecule can be detected directly. Detection of binding is preferably done for screening purposes, preferably in a high throughput setting. Preferred screening purposes are screening for compounds that affect the binding of the peptide to the MHC molecule. For instance, test peptides or small molecules can compete with binding of the peptide to the MHC molecule. Competition can be detected by detecting decreased binding of the peptide. A preferred method for detecting binding of the peptide to the MHC molecule is measured by means of fluorescence anisotropy. In this way, manipulations of the sample wherein binding is performed can be reduced. Reduction of sample manipulations is a desired property for high throughput settings. Other preferred means for detecting binding of the peptide are monitoring radioactivity or by monitoring binding of an MHC conformation-dependent binding body, preferably an antibody or a functional part, derivative and/or analogue thereof. Other preferred means include the use of a T-cell receptor specific for the combination of the peptide, MHC molecule.

In a preferred embodiment, inhibition or enhancement of binding of the peptide to the MHC molecule is measured. In a preferred embodiment, the method is used for determining binding of the desired peptide in the presence of a test or reference compound.

The invention further provides an MHC molecule obtainable by a method of the invention. Further, the invention provides a composition comprising an MHC molecule according to the invention, wherein the composition comprises an MHC molecule complex comprising a peptide comprising a conditionally reactive group or a derivative thereof and an MHC molecule complex comprising a further peptide.

Multimers of the invention may further be incorporated into even larger structures that are further referred to as complexes of MHC multimers or as MHC tetramers, to distinguish them from the multimers of the invention. Such complexes have a higher affinity for the particles and cells carrying T-cell receptors than the single MHC multimer. Such complexes are, therefore, important tools in the analysis of T-cell populations. The invention thus further provides a complex comprising at least two multimers of the invention or at least two MHC molecules or functional parts, derivatives and/or analogues thereof of the invention or a combination thereof. Means and methods for producing complexes containing two, three, four and five MHC molecules or functional parts, derivatives and/or analogues thereof are available in the art. Thus, the present invention further provides a complex comprising two, three, four or five MHC molecules or functional parts, derivatives and/or analogues thereof.

In a preferred embodiment, the complexes comprise MHC molecules having the same T-cell receptor specificity. However, this need not always be the case. Considering the relative ease with which MHC molecules can be provided with different peptides using a method of the invention, complexes comprising two or more T-cell receptor specificities are within the scope of the present invention.

The invention further provides a solid surface comprising at least two multimers according to the invention, a composition according to the invention or an MHC molecule or functional part, derivative and/or analogue of the invention. In a preferred embodiment, the solid surface is provided with a complex of the invention, preferably a complex comprising a single peptide, or multiple peptides associated with the same disease or pathogen. The solid surface can be a bead. The solid surface can be a glass or metallic surface. The surface may have undergone pre-treatment prior to coating of the multimer, composition or complex of the invention. Such pre-treatment may include, but is not limited to, polyacrylamide film coating as described by Soen et al. (PLoS Biology, 2003: vol. 1, pages 429-438).

The invention further provides a microarray comprising a multimer, composition or complex of the invention. Means and methods for producing a (micro)array comprising an MHC molecule complex coupled to antigenic peptide is described by Soen et al. mentioned above. The artisan is referred to that reference for guidance as to the generation of a (micro)array of the invention.

The invention surprisingly found a novel influenza A nucleoprotein T-cell epitope in an H5N1 strain. The novel epitope interestingly has a substantially greater immunogenicity than a classical epitope found in H5N1 strains and many other influenza A strains. Furthermore, the novel epitope is shared between H5N1 strains of the past years but is distinct from older influenza A strains, which makes it an epitope that is more suitable for present and future diagnostic and therapeutic purposes than classic epitopes.

The invention provides peptides comprising the H5N1 epitope sequence. The invention, therefore, provides an isolated and/or synthesized peptide comprising amino acid sequence AMDSNTLEL (SEQ ID NO:1). Further, the invention provides the use of an isolated and/or synthesized peptide comprising amino acid sequence AMDSNTLEL (SEQ ID NO:1) in a vaccine. Also provided is the use of an isolated and/or synthesized peptide comprising amino acid sequence AMDSNTLEL (SEQ ID NO:1) for the preparation of a vaccine against influenza. A peptide of the invention is, for instance, presented to the immune system of an individual in a vaccine comprising the peptide and an immune-enhancing agent.

In one embodiment, the invention provides a method for immunizing an individual against influenza, comprising providing the individual with an isolated and/or synthesized peptide comprising an amino acid sequence AMDSNTLEL (SEQ ID NO:1) and optionally an immune-enhancing agent and/or a suitable additive. "Immunizing an individual" as used herein means that the individual develops an immune response against the peptide. The invention further provides a fusion protein comprising a peptide comprising the amino acid sequence AMDSNTLEL (SEQ ID NO:1). The invention further provides a nucleic acid encoding the AMDSNTLEL (SEQ ID NO:1) peptide or the fusion protein.

The invention in one embodiment provides an MHC molecule according to the invention, comprising an isolated and/or synthesized peptide comprising amino acid sequence AMDSNTLEL (SEQ ID NO:1). In one embodiment of the invention, the MHC molecule according to the invention is for the detection of epitope-specific T-cells. The influenza is preferably H5N1. An influenza virus to diagnose is preferably a current variant of an influenza virus.

In one embodiment, the invention provides the use of an MHC molecule according to the invention for the preparation of a composition for diagnosing influenza. In a further embodiment, the invention provides a method for diagnosing influenza in an individual, comprising providing a blood sample of the individual with an MHC molecule according to the invention and analyzing binding of the MHC molecule to a cell in the blood sample. The cell in the blood sample is preferably a T-cell. In a preferred embodiment, a method for diagnosing influenza in an individual further comprises detecting a T-cell response.

BRIEF DESCRIPTION OF THE DRAWINGS

FIG. 1. Photocleavage strategy.

FIG. 2. Biochemical analysis of UV-induced peptide exchange.

DETAILED DESCRIPTION OF THE INVENTION

Examples

Methods

Production of MHC Multimers and Complexes of MHC Multimers (MHC Tetramers):

MHC class I complexes (MHC multimers) were prepared as previously described with minor modifications.[1] HLA-A2.1-peptide multimers were generated with the following three peptides: Influenza-A matrix 58-66 (sequence GILGFVFTL (SEQ ID NO:2)) and the two influenza A matrix 58-66 variants GIL*FVFTL (SEQ ID NO:3 and GILGFVF*L (SEQ ID NO:4) where * is 3-amino-3-(2-nitrophenyl)propionic acid. MHC class I-peptide multimers were subsequently purified, biotinylated by BirA, purified and stored at −20° C. in 16% glycerol.

UV-Induced Peptide Liberation and Peptide Exchange:

MHC multimers or, where indicated, tetrameric complexes of MHC multimers containing the wild-type influenza A matrix 58-66 epitope, or the G4* or T8* variants of this epitope, were exposed for one huor to UV (CAMAG, 366 nm) in 20 mM Tris-HCl, pH 7.0/150 mM NaCl/0.5 mM dithiothreitol (DTT) in the presence or absence of MHC class I binding peptides. Subsequently, the complex was exposed to 37° C. for 15-45 minutes to induce dissociation of peptide-free MHC class I complexes.[2] Samples were then analyzed by gel filtration chromatography to determine MHC dissociation, or were incubated with phycoerythrin-labeled streptavidin to generate tetrameric complexes of MHC multimers (MHC tetramers). MHC tetramers were purified by gel filtration chromatography and stored at −20° C. in 16% glycerol until further use.

MHC Tetramer Staining:

Thawed peripheral blood mononuclear cells (PBMC) samples and CTL clones were incubated for five minutes with PE-labeled MHC tetramers at 37° C., FITC-labeled anti-CD8 antibody was added and incubation was continued for 15 minutes at room temperature. Prior to FACS analysis, cells were stained with propidium iodide to be able to gate out dead cells. Samples were analyzed by flow cytometry using a FACScalibur and CellQuest software (Becton Dickinson). Forward and side scatter parameters were used to define lymphocyte populations.

Results:

Formation of Peptide-MHC Multimers that Dissociate at Will.

Figure 1A:
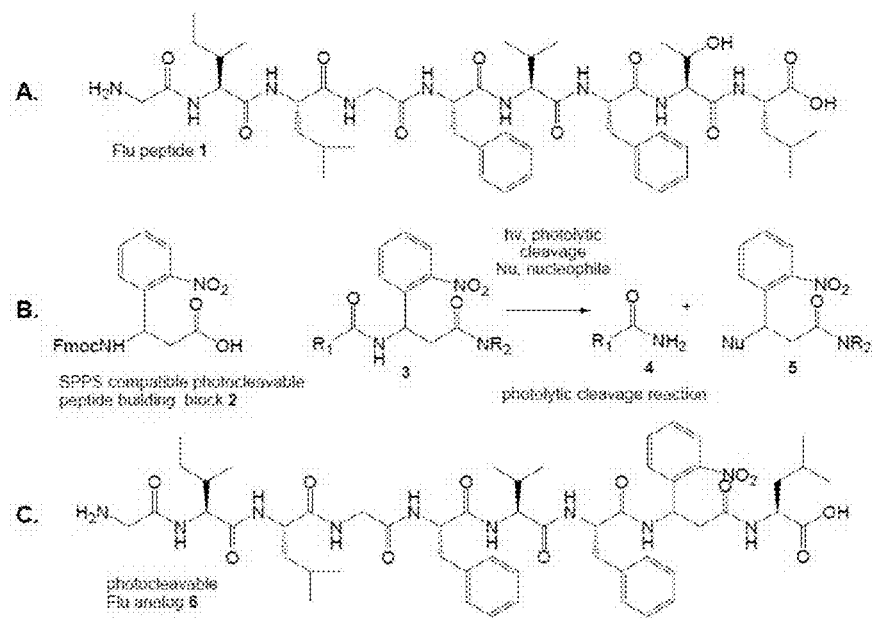
FIG. 1A (A), Structure of I, the unmodified influenza A 58-66 epitope (sequence GILGFVFTL (SEQ ID NO:2)); (B), Photocleavage reaction. (C), The structure of III is the T8*-modified photocleavable influenza A 58-66 epitope (sequence GILGFVF*L (SEQ ID NO:4) where * is 3-amino-3-(2-nitrophenyl) propionic acid). Oxidative periodate cleavage strategy.
Figure 1B:
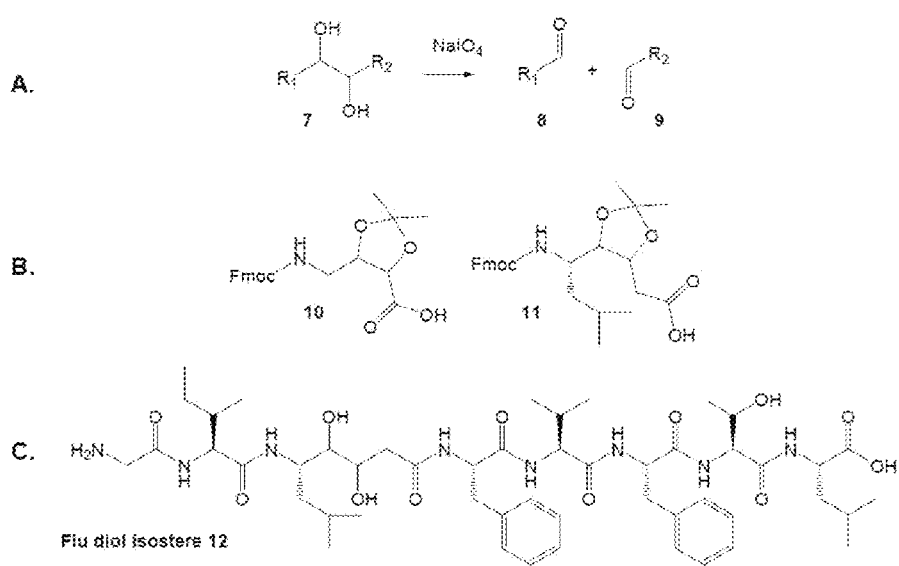
FIG. 1B (A) Cleavage reaction. (B) Building blocks. (C) Structure of periodate cleavable flu peptide (sequence GI*GFVFTL (SEQ ID NO:6) where * is a dipeptide isostere).

To test the feasibility of generating MHC multimers of which the bound peptide could be liberated at will, we generated HLA-A2.1 multimers with either the wild-type influenza A matrix 58-66 epitope, or two variants of this epitope in which either amino acid 4 or amino acid 8 was replaced by the UV-sensitive beta-amino acid 3 (FIG. 1). MHC class I multimer formation was efficient for all three peptides and the multimers formed were purified by gel filtration chromatography. To assess whether the resulting peptide-MHC multimers could be induced to dissociate, the three types of multimers were exposed to UV, incubated at 37° C. to induce dissociation of remaining peptide-free MHC class I molecules and then analyzed by gel filtration chromatography.

Figure 2A:
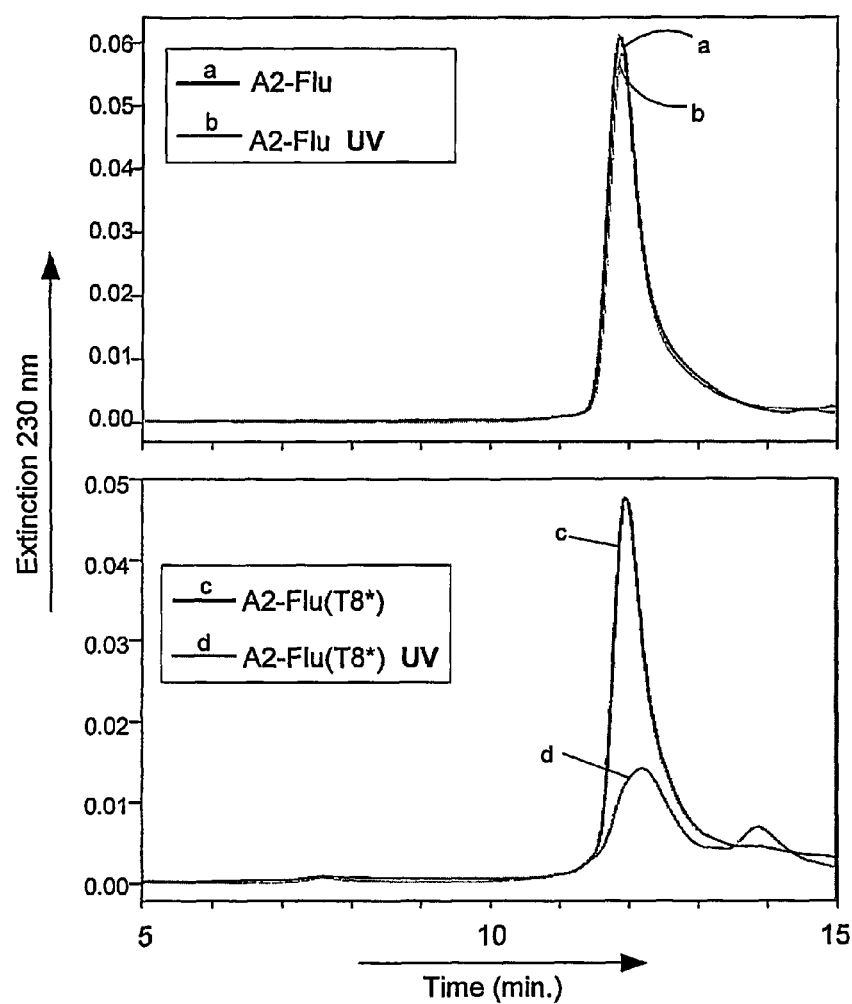
FIG. 2A, MHC multimers containing a UV-sensitive ligand are sensitive to UV exposure.

Whereas, the peptide-MHC multimer containing the parental influenza A epitope is fully insensitive to UV exposure (FIG. 2A top panel), exposure of MHC class I multimers containing either the G4* (data not shown) or the T8* epitope (FIG. 2A bottom panel) leads to a substantial reduction in the amount of MHC complex recovered. Furthermore, the remaining material most likely consists, at least in part, of free MHC class I heavy chains rather than peptide-MHC class I multimers, as suggested by the fact that the elution time of remaining material is slightly greater than that of the starting material.

Protection of MHC Class I Dissociation by Addition HLA-A2.1-Binding Peptides.

Figure 2B:
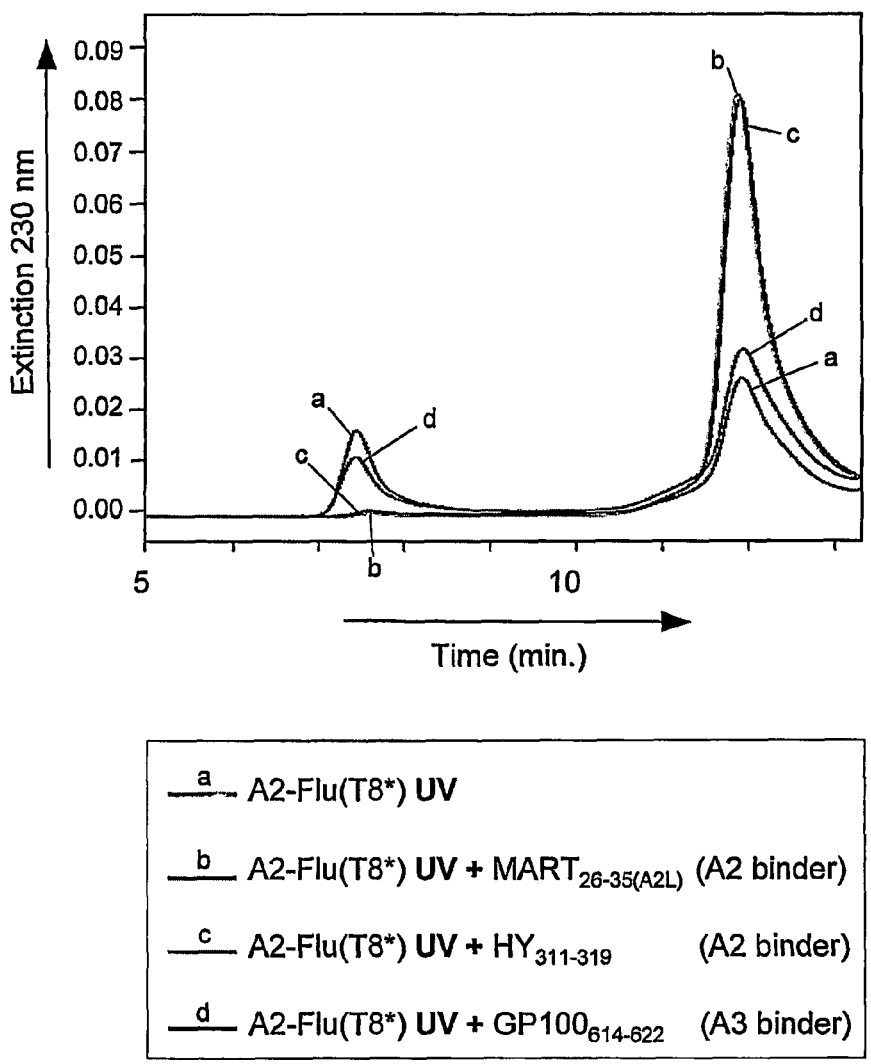
FIG. 2B, UV-sensitive MHC multimers that are exposed to UV can be stabilized by addition of MHC-binding peptides.

To assess whether the addition of MHC class I binding ligands could protect the dissociation of UV-sensitive MHC complexes upon UV exposure, the same reactions were performed either in the presence of one of two different HLA-A2.1-binding peptides (HY 311-319; MART I 26-35 (A2L mutant), or the HLA-A3-binding peptide GP100 (614-622). Addition of either of the three peptides to MHC class I molecules containing the parental influenza A epitope does not affect the recovery of the MHC class I multimer, regardless of whether the multimer is exposed to UV, consistent with the notion that this parental MHC multimer is stable under both conditions (data not shown). Importantly, while addition of the HLA-A3-binding peptide that is not expected to interact with HLA-A2.1 does not lead to a substantial increase in the recovery of the UV-sensitive G4* (not shown) or T8* peptide-containing (FIG. 2B) MHC multimer, the addition of either HLA-A2.1-binding peptide leads to a highly increased recovery (FIG. 2B). These data are consistent with the notion that the peptide-free MHC molecules that are generated upon exposure of the G4*- or T8*-containing MHC multimer to UV can efficiently bind known HLA-A2.1 ligands but not a control peptide.

Functional Tetrameric Complexes of MHC Multimers Generated from UV-Sensitive MHC Multimers.

Figure 3:
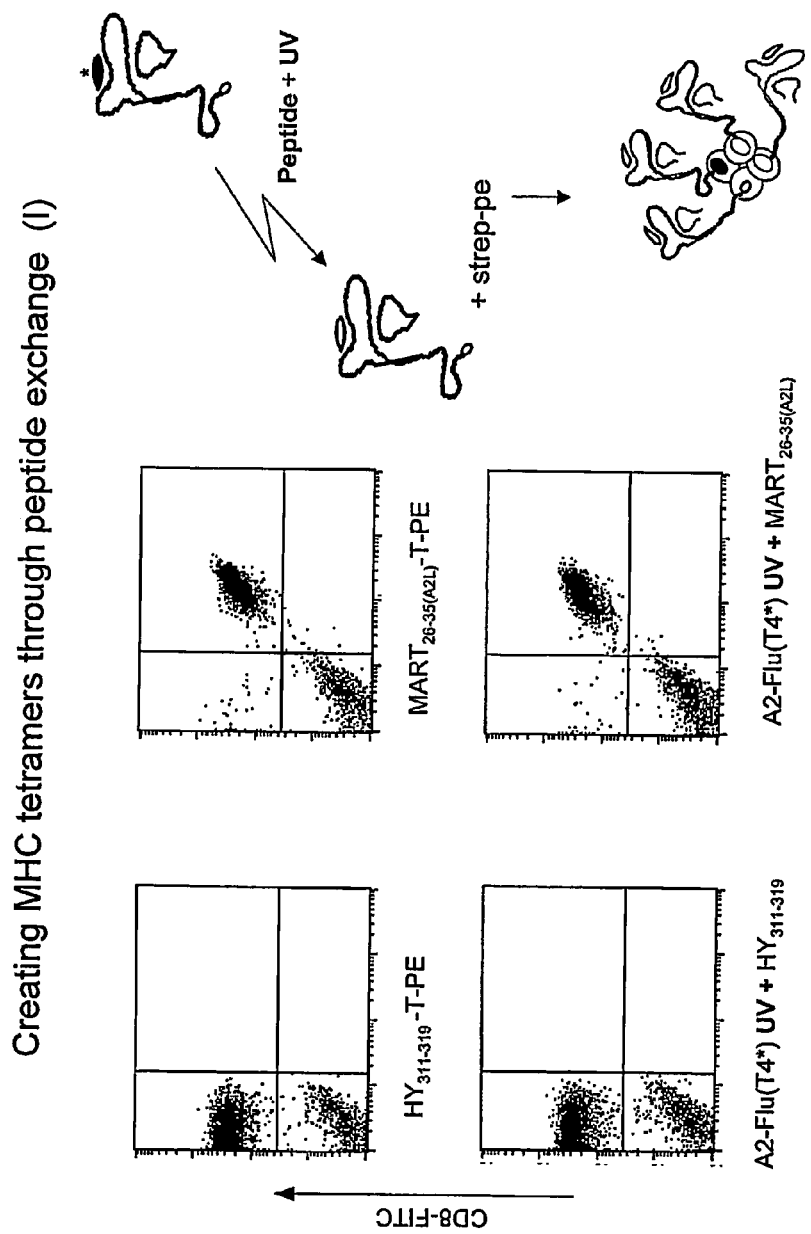
FIG. 3. MHC tetramers generated from UV-sensitive MHC multimers stain an antigen-specific CTL clone. UV-sensitive MHC multimers were exposed to UV in the presence of the indicated peptides and were converted to tetrameric complexes of MHC multimers. Thus generated tetramers containing either the HY (SMCY) 311-319 peptide (lower left panel) or MART I 26-35 (A2L mutant) peptide (lower right panel) were used to stain a MART I 26-35-specific CTL clone. As a control, the same clone was stained using classical MHC class I tetramers containing the same epitopes (top panels).
Figure 4:
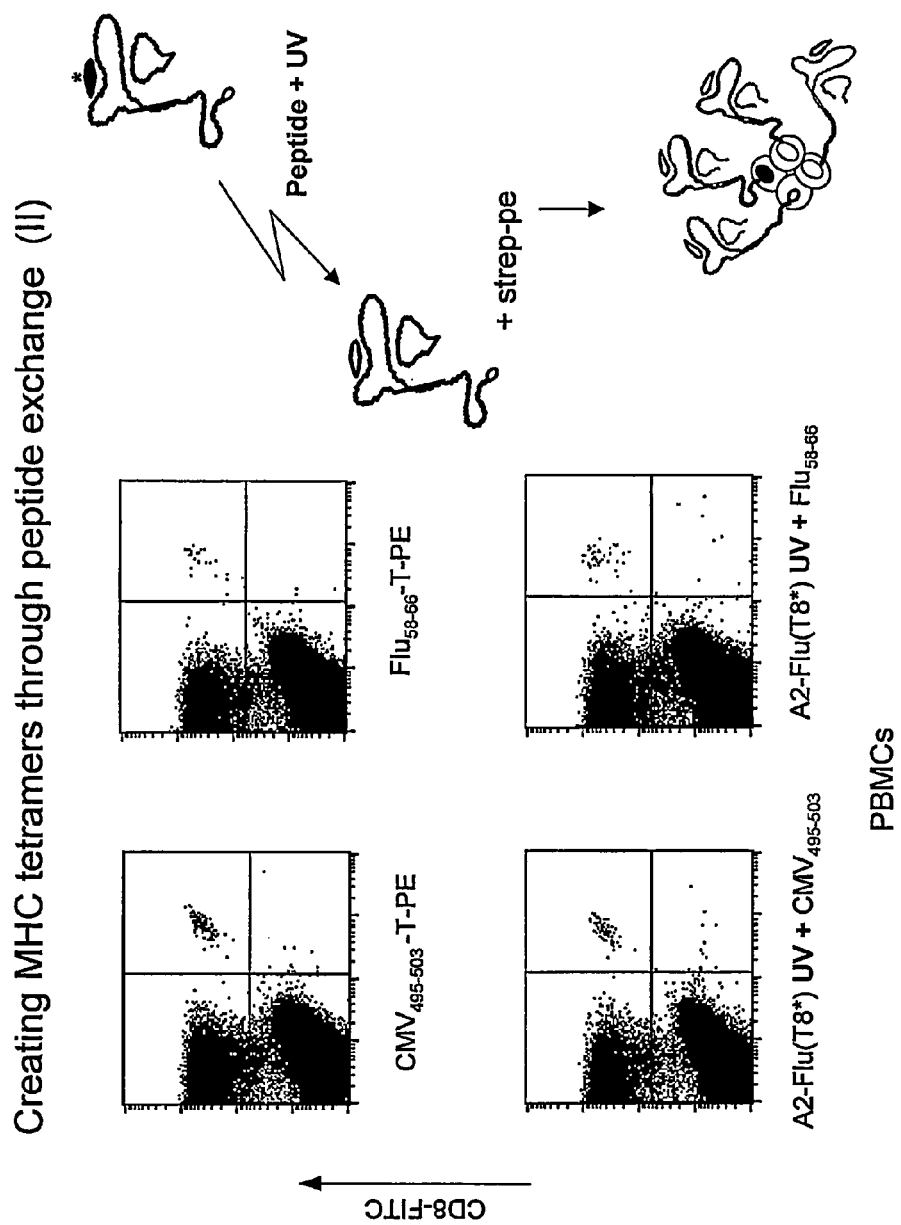
FIG. 4. MHC tetramers generated from UV-sensitive MHC multimers stain antigen-specific peripheral blood T-cells. UV-sensitive MHC multimers were exposed to UV in the presence of the indicated peptides and were converted to MHC tetramers. Thus generated tetramers containing either the CMV pp65 495-503 peptide (lower left panel) or influenza A matrix 58-66 peptide (lower right panel) were used to stain peripheral blood mononuclear cells from a donor with both CMV pp65 495-503 and influenza A matrix 58-66-specific CD8+ T-cells. As a control, the same PBMCs were stained using classical MHC class I tetramers containing the same epitopes (top panels).

To directly establish whether the UV-sensitive MHC class I multimers that had been protected by addition of HLA-A2.1 ligands had bound these ligands, MHC multimers generated in the presence of either the MART I 26-35 (A2L mutant), influenza A matrix 58-66, HY (SMCY) 311-319, or CMV pp65 495-503 peptide were purified and converted to tetrameric complexes of MHC multimers. The resulting MHC tetramers were subsequently used to stain either a MART I-specific T-cell clone (FIG. 3) or peripheral blood mononuclear cells from a donor with both CMV pp65 495-503 and influenza A matrix 58-66-specific CD8+ T-cells (FIG. 4). In all cases tested, MHC tetramers generated following peptide exchange bind antigen-specific T-cells with equal sensitivity and specificity as compared to conventional MHC tetramers. These experiments provide formal proof that MHC multimers generated by peptide exchange are structurally indistinguishable from conventional peptide-MHC multimers and can be used to probe pMHC-TCR interactions, in this case following oligomerization.

Functional MHC Tetramers Generated from UV-Sensitive MHC Tetramers.

Figure 5:
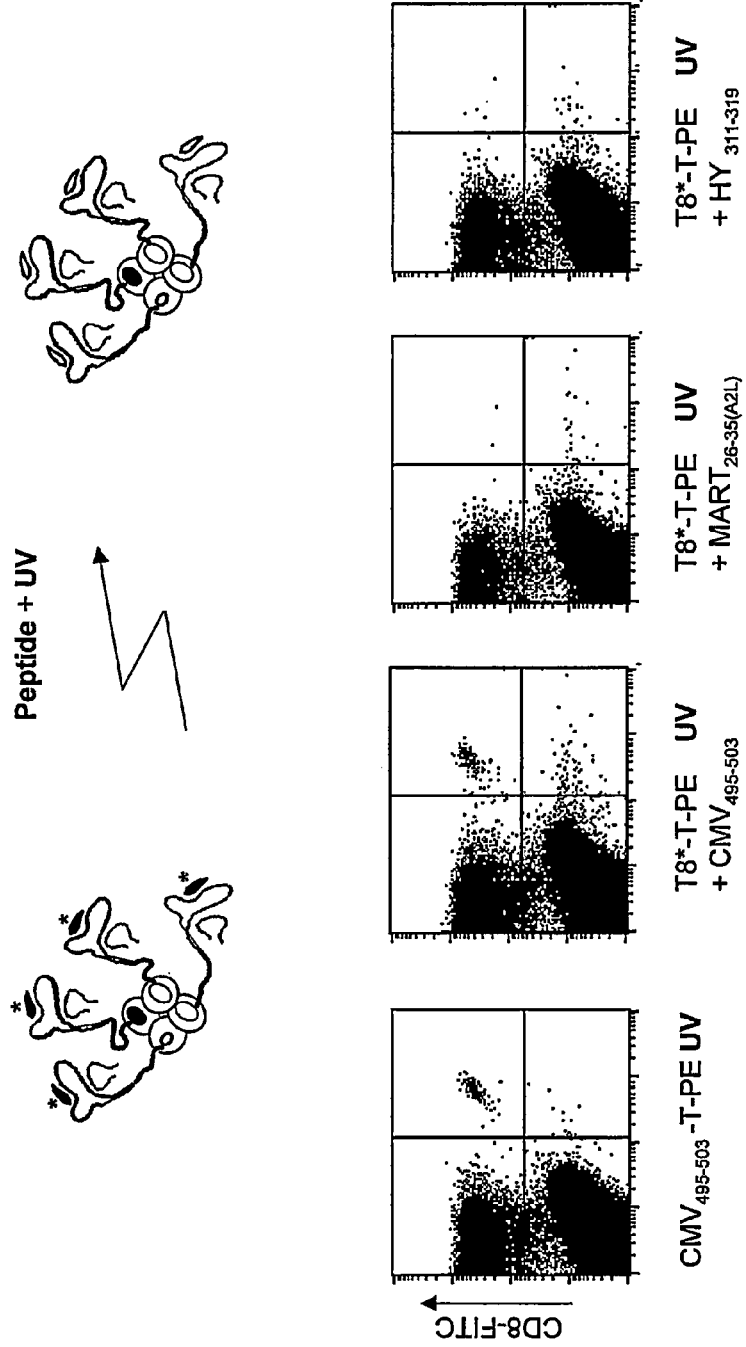
FIG. 5. MHC tetramers generated from UV-sensitive MHC tetramers stain antigen-specific peripheral blood T-cells. UV-sensitive MHC tetramers were exposed to UV in the presence of the indicated peptides and were used to stain antigen-specific T-cells without further purification. MHC tetramers containing either the CMV pp65 495-503 peptide (second left panel), or MART I 26-35 (A2L mutant) or HY (SMCY) 311-319 peptide (two right-most panels) were used to stain peripheral blood mononuclear cells from a donor with CMV pp65 495-503 CD8+ T-cells. As a control, the same PBMCs were stained using classical MHC class I tetramers containing the CMV pp65 495-503 peptide (left panel).

To establish whether peptide exchange could also be performed on UV-sensitive tetrameric complexes of MHC class I multimers, T8*-containing MHC multimers were converted to tetrameric complexes and subsequently exposed to UV in the presence of either the CMV pp65 495-503, MART I 26-35 (A2L mutant), or HY (SMCY) 311-319 peptide. The resulting tetrameric MHC complexes were subsequently used without further purification to stain peripheral blood mononuclear cells of a CMV-positive donor. Remarkably, MHC tetramers generated by UV exposure of T8*-containing MHC tetramers in the presence of the CMV pp65 495-503 epitope detect CMV-specific T-cells at an equal frequency and with similar intensity as conventional CMV pp65 495-503-specific MHC tetramers (FIG. 5). The specificity of this binding is underscored by the fact that MHC tetramers prepared in parallel reactions with either the MART I 26-35 (A2L mutant), or HY (SMCY) 311-319 peptide do not show measurable binding to CD8+ lymphocytes of this donor.

Other Aspects of MHC Exchange Technology.

Figure 6:
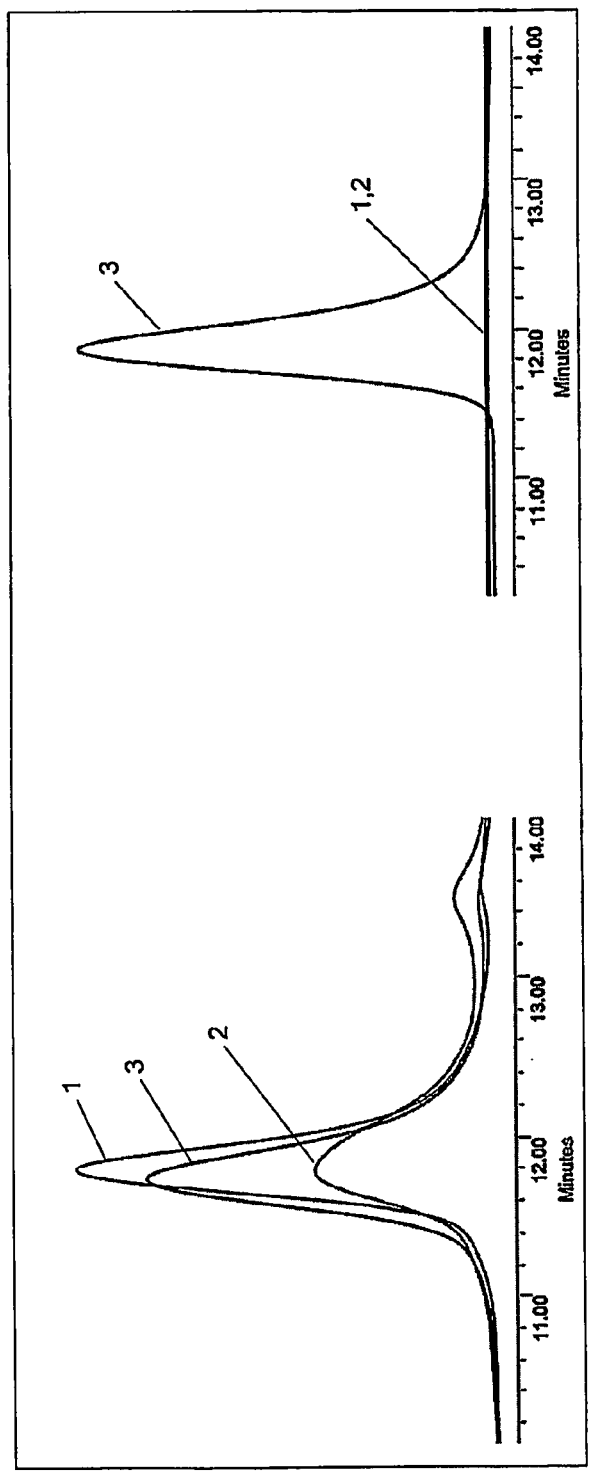
FIG. 6. Gel filtration profile of photolabile peptide/HLA-A2.1 complex before irradiation (1), after irradiation without rescue (2), after irradiation in the presence of peptide FLPSDC*FPSV (SEQ ID NO:5) where C* is labeled with a tetramethylrhodamine dye (3). Left panel: UV detection at 230 nm; Right panel: Fluorescence detection (excitation 530 nm, emission 550 nm).
Figure 7:
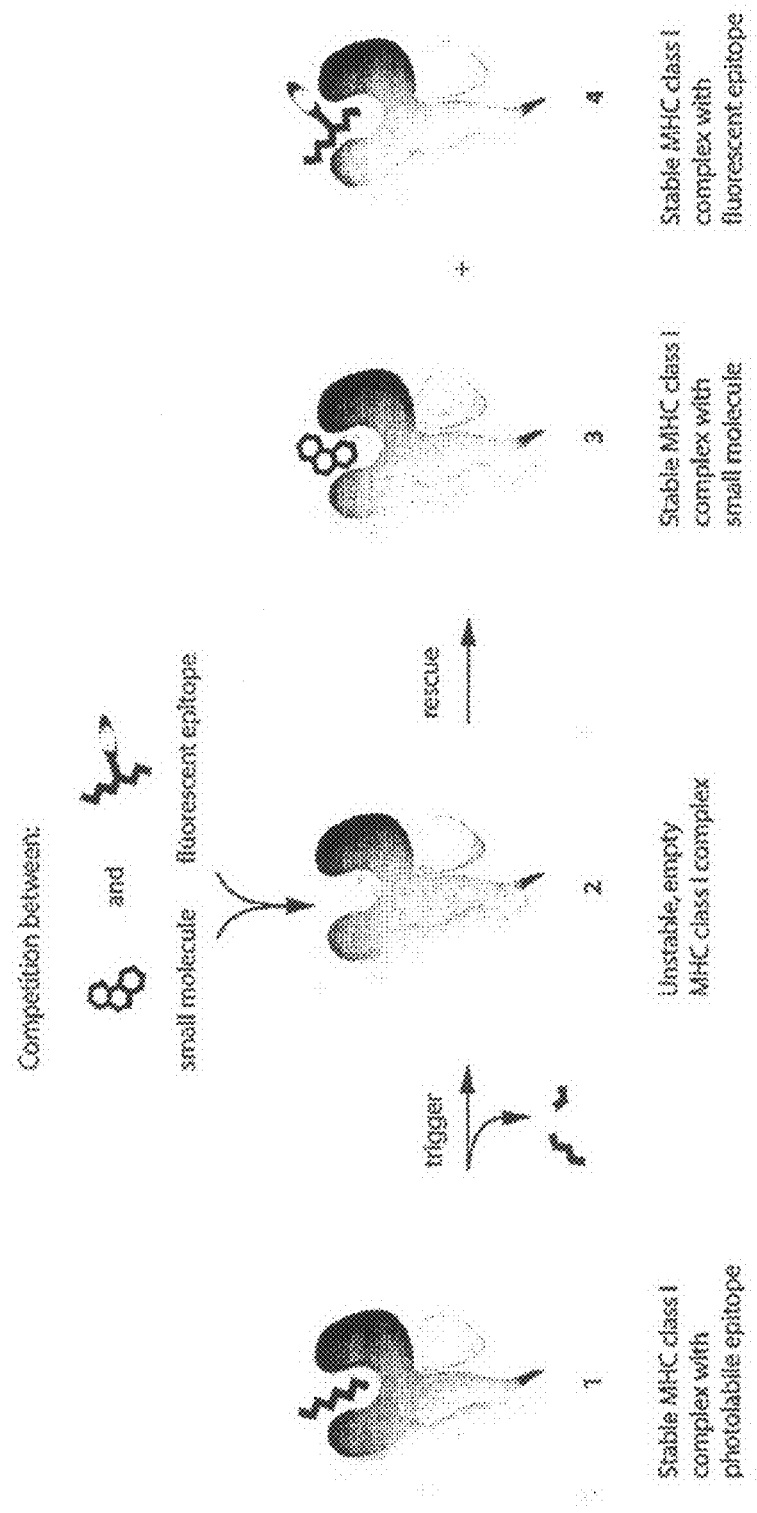
FIG. 7. Fluorescence anisotropy screen. Peptide-free MHC molecules are generated by cleavage of the conditional ligand. The binding of a fluorescent epitope is monitored by measurement of fluorescence anisotropy or fluorescence detection. By this method, peptidic or non-peptidic ligands that interfere with or facilitate such binding can be identified.

UV exchange technology was used to generate MHC molecules that are receptive to binding of ligands that carry a label. MHC exchange reactions were carried out in the presence of a peptide ligand that had been labeled with a tetramethylrhodamine dye. As shown in FIG. 6, subsequent analysis of these reactions reveals that this technology can be used to allow binding of a labeled ligand, in this case a fluorescent peptide. Consequently, MHC exchange technology can also be used to screen for compounds (e.g., peptides and other small molecules) that can enhance or interfere with such binding. The principle of such a screen, here exemplified using fluorescence anisotropy, is outlined in FIG. 7.

Figure 8A:
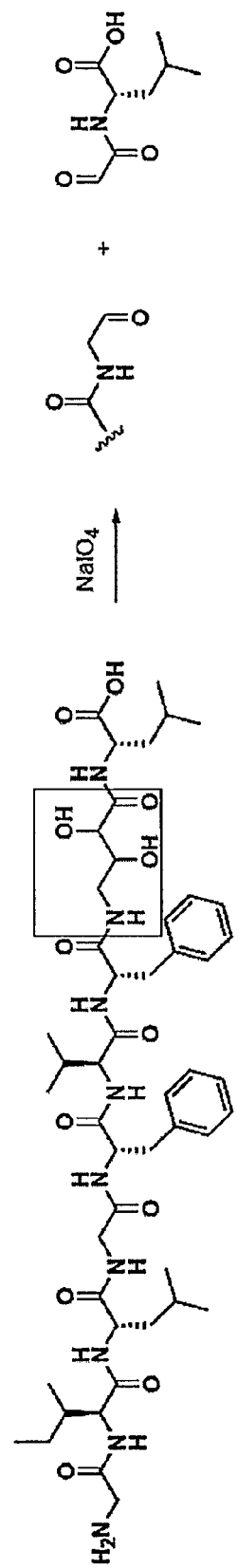
FIG. 8. 8A. Diol-based chemocleavable conditional peptide (sequence GILGFVF*L (SEQ ID NO. 7) where * is 4-amino-2,3-dihydroxybutanoic acid) and the corresponding cleavage products. The diol-containing unit is boxed. 8B. Oxidative periodate mediated peptide cleavage.
Figure 8B:
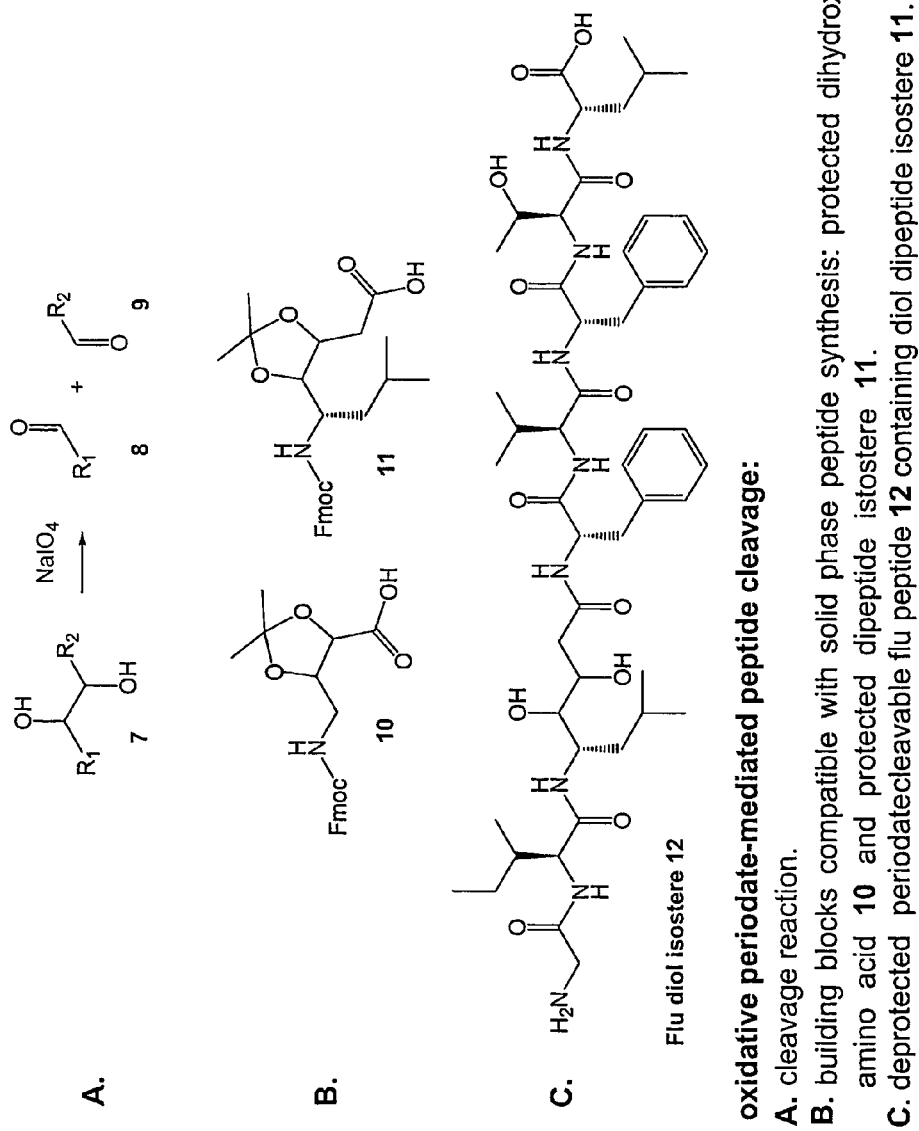
Figure 9:
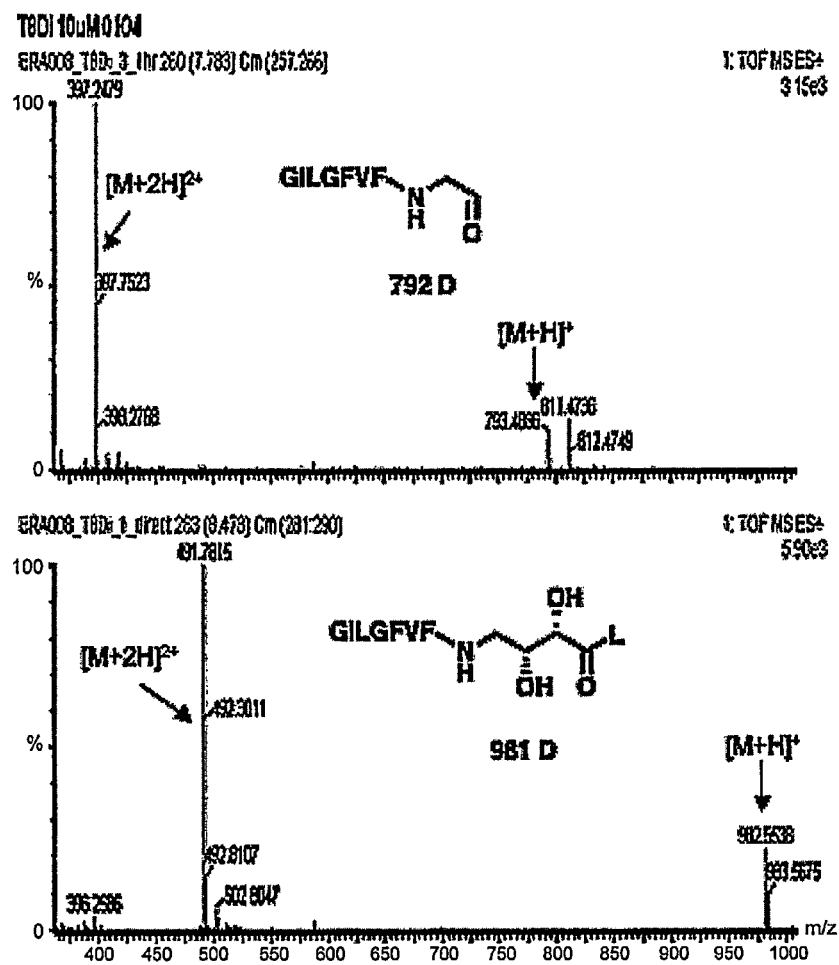
FIG. 9. Cleavage of MHC-binding peptides by NaIO4. Peptide variants of the HLA-A2.1-binding M1 peptide with a diol-containing building block at position 8 (FIG. 8A) or position 4 (not shown) were produced by chemical synthesis. Peptides were then analyzed by LC-MS, prior to (bottom, sequence GILGFVF*L (SEQ ID NO. 7) where * is 4-amino-2,3-dihydroxybutanoic acid) or following (top) a one hour exposure to 1 mM NaIO4.

Modification of known MHC-binding peptides allows the generation of ligands that are sensitive to chemical cleavage, variants of the influenza A matrix 58-66 peptide were produced in which a diol-containing building block is incorporated. An example of such a modified ligand is given in FIG. 8. Exposure of such modified ligands to periodate leads to cleavage of these ligands, as exemplified in FIG. 9.

Discussion:

The current data describe a novel approach for the generation of MHC complexes that are occupied with a peptide of choice. The main limitation in the production of such complexes has been the instability of peptide-free MHC molecules. Consequently, the technology that is now widely accepted for the generation of recombinant MHC molecules is the separate production of a batch of ligand-occupied MHC molecules for each single ligand. This results in a very time-consuming and costly production process, yielding small batches specific for only one application. Here, we demonstrate that MHC molecules occupied by a ligand of choice can be generated by the selective release of a previously bound ligand, by exposure to conditions that do not directly affect the stability of the MHC complex itself.

In the current set of experiments, dissociation of MHC-bound ligand was achieved through the use of a light-sensitive peptide variant. However, it is apparent that such dissociation may equally well be achieved through the use of peptide variants that are sensitive to other defined conditions. In particular, the development of peptide-MHC complexes using peptide variants that are sensitive to chemical cleavage appear useful in this respect. In addition, dissociation may also be achieved without peptide cleavage, by inducing a reduced affinity of the bound ligand for MHC through chemical- or light-induced modification. Furthermore, while the approach for ligand exchange has here been developed for MHC class I molecules, this approach should be equally useful to prepare ligand-occupied MHC class II molecules or non-classical MHC molecules (exemplified by CD1 and Qa1 molecules).

Recombinant MHC molecules generated through chemical- or light-induced peptide release will be of substantial use to generate the vast collections of MHC complexes that are currently used in clinical and preclinical research. In addition, the ability to generate MHC ligands occupied by a desired ligand through simple exchange should greatly facilitate efforts to produce GMP grade MHC molecules that can be used for selective antigen-specific T-cell depletion or enrichment. Finally, the ability to perform peptide exchange on preformed MHC complexes forms a viable strategy to generate microarrays of MHC complexes occupied with large collections of peptide antigens. Such MHC microarrays may form useful tools for the high throughput analysis of the antigen-specific T-cell repertoire.[3]

REFERENCES

Altman J. D., P. A. Moss, P. J. Goulder, D. H. Barouch, M. G. McHeyzer-Williams, J. I. Bell, A. J. McMichael and M. M. Davis. Phenotypic analysis of antigen-specific T-lymphocytes. Science 274:94-96 (1996).
2. Schumacher T. N. M., M.-T. Heemels, J. J. Neefjes, W. M. Kast, C. J. M. Melief, and H. L. Ploegh. Direct binding of peptide to empty MHC class I molecules on intact cells and in vitro. Cell 62:563-567 (1990).
3. Soen Y., D. S. Chen, D. L. Kraft, M. M. Davis M M, and P. O. Brown. Detection and Characterization of Cellular Immune Responses Using Peptide-MHC Microarrays. PLoS Biol. 1:E65: pp. 429-438 (2003).
4. Parmiani G., A. Testori, M. Maio, C. Castelli, L. Rivoltini, L. Pilla, F. Belli, V. Mazzaferro, J. Coppa, R. Patuzzo, M. R. Sertoli, A. Hoos, P. K. Srivastava and M. Santinami. Heat shock proteins and their use as anticancer vaccines. Clinical Cancer Research 10:8142-8146 (2004).

The invention claimed is:

1. A method for producing a major histocompatibility complex (MHC) molecule, said method comprising:
    providing a major histocompatability complex (MHC) molecule with a temporary peptide that binds to the peptide-binding groove of the MHC molecule, wherein the temporary peptide has at least one reactive group, wherein the reactive group is a light-sensitive group or a periodate-sensitive group, and wherein the reactive group, when activated, cleaves the temporary peptide into at least two peptides that each exhibit reduced binding affinity for the MHC molecule, with respect to the uncleaved temporary peptide.

2. The method according to claim 1, further comprising:
    activating the reactive group so as to cleave the temporary peptide into the at least two peptides.

3. The method according to claim 2, further comprising:
    providing the MHC molecule with a desired peptide that binds to the MHC molecule's peptide-binding groove.

4. The method according to claim 3, further comprising:
    incubating the MHC molecule with the desired peptide under conditions that remove cleaved peptide from the MHC molecule.

5. The method according to claim 1, wherein the light-sensitive group comprises 3-amino-3-(2-nitrophenyl)propionic acid.

6. The method according to claim 1, wherein the periodate-sensitive group comprises a 1,2-dihydroxy moiety.

7. The method according to claim 3, further comprising detecting the binding of said desired peptide to said MHC molecule.

8. The method according to claim 7, wherein said binding is detected by detecting a label that is associated with said peptide.

9. The method according to claim 8, wherein said peptide comprises said label.

10. The method according to claim 7, wherein said binding of said peptide to said MHC molecule is measured by fluorescence anisotropy.

11. The method according to claim 7, wherein binding of said desired peptide is determined in the presence of a test or reference compound.

\* \* \* \* \*